US008679807B2

(12) United States Patent
Oscarsson et al.

(10) Patent No.: US 8,679,807 B2
(45) Date of Patent: Mar. 25, 2014

(54) COVALENT IMMOBILIZATION OF MOLECULES COMPRISING AN AMINO GROUP

(75) Inventors: Sven Oscarsson, Uppsala (SE); Kristofer Eriksson, Eskilstuna (SE); Leif Nyholm, Uppsala (SE)

(73) Assignee: Lab-On-A-Bead, Lycke (SE)

( * ) Notice: Subject to any disclaimer, the term of this patent is extended or adjusted under 35 U.S.C. 154(b) by 0 days.

(21) Appl. No.: 13/812,101

(22) PCT Filed: Jul. 27, 2011

(86) PCT No.: PCT/EP2011/062865
§ 371 (c)(1),
(2), (4) Date: Apr. 3, 2013

(87) PCT Pub. No.: WO2012/013693
PCT Pub. Date: Feb. 2, 2012

(65) Prior Publication Data
US 2013/0197195 A1    Aug. 1, 2013

Related U.S. Application Data

(60) Provisional application No. 61/368,076, filed on Jul. 27, 2010.

(30) Foreign Application Priority Data

Jul. 27, 2010 (SE) ...................................... 1050833

(51) Int. Cl.
*C12N 11/00*     (2006.01)
*C12N 11/06*     (2006.01)
*C12N 11/04*     (2006.01)

(52) U.S. Cl.
USPC ............................ 435/174; 435/180; 435/181

(58) Field of Classification Search
USPC .......................................... 435/174, 180, 181
See application file for complete search history.

(56) References Cited

FOREIGN PATENT DOCUMENTS

WO    2009/074692 A2    6/2009

OTHER PUBLICATIONS

Shervedani et al, Electrochimica Acta 53:4185-4192 (2008).
Burgener et al, Bioconjugate Chem, 11:749-754 (2000).
El-Nahhal et al, Journal of Organometallic Chemistry, 692:2861-2886 (2007).
Pavlovic et al, Langmuir, 19:4217-4221 (2003).
Haruyama et al, Biomaterials, 26:4944-4947 (2005).

*Primary Examiner* — Maryam Monshipouri
(74) *Attorney, Agent, or Firm* — Porter Wright Morris & Arthur LLP

(57) ABSTRACT

There is provided a method for covalent immobilization of at least one molecule comprising at least one amino group, said method comprising the sequential steps of: a) providing a surface comprising —SH groups, b) oxidizing the surface comprising —SH groups using redox reactions in the presence of noble metal ions, and c) contacting the surface with at least one molecule comprising at least one amino group to obtain a covalent binding of the at least one molecule to the surface, wherein said at least one amino group is involved in obtaining said covalent bond. The immobilized molecules are immobilized via stable covalent bonds. The method is more versatile since it can be performed as a one step method. All reaction steps are performed in aqueous solution. All steps can be performed at room temperature. The chemicals used are less expensive and less toxic compared to the prior art.

19 Claims, 2 Drawing Sheets

COVALENT IMMOBILIZATION OF MOLECULES COMPRISING AN AMINO GROUP

This application is a 371 of PCT/EP11/62865, filed Jul. 27,2011, which claims domestic and foreign priority to the following applications: 61/368,076, and Swedish application 1050833-1 , respectively, both filed Jul. 27,2010.

TECHNICAL FIELD

The present invention relates generally to covalent immobilization of molecules comprising at least one amino group.

BACKGROUND

Techniques for covalent immobilization of molecules on surfaces are of crucial importance in surface science. For instance immobilized enzymes possess many benefits which include that no or only extremely small amount of immobilized enzyme dissolves in the reaction. Upon completion, reaction mixtures typically contain only solvent and reaction products. The immobilized enzyme is easily removed from the reaction making it easy to recycle.

Examples include but are not limited to areas such as catalysis, biosensors, microcontact printing, chromatography, and analytical devices. Several immobilization techniques are available today, for instance based on silanol chemistry, click chemistry, and one commonly used method for immobilization of biomolecules, the so called NHS (N-hydroxysuccinimid) method. Drawbacks for all those techniques include unstable bonds between immobilized molecules and the surface, expensive toxic chemicals or a prerequisite for organic solvents during the introduction of reactive structures on the surfaces.

The most used technique today is the so called NHS (N-hydroxysuccinimide) coupling technique. One of several disadvantages with this technique has been described by e.g. Wilchek. According to the latter author, this method is known to yield unstable bonds especially for single point attached molecules. It has e.g. been reported that 50% of the alanine immobilized by this method can be lost in 40 days (Cuatrecasas et al. in Biochemistry, vol. 11, p. 2291, 1972). According to Wilchek et al. in Biochemistry, vol. 26, p. 2155, 1987 the standard procedure to prepare NHS esters (namely N-hydroxysuccinimide and carbodiimides) leads to the formation of unstable immobilized compounds on polymers that also contain hydroxyl groups. This phenomenon is due to the formation of a p-alanine derivative which binds to the hydroxy-containing polymer, resulting in an unstable bond.

Other disadvantages of the NHS technique include that the ester bond which is used for covalent immobilization of molecules such as alanine or IgG will compete with the hydrolysis of the ester in aqueous media and that anhydrous conditions must be used in some steps for preparation of this final ester bond which involves use of dioxane. Step 1 in this process is the immobilization of a diamine (3,'3 diaminodipropylcarbodiimide) to the matrix followed in step 2 by intense washing with dioxane to be able to create anhydrous conditions for the next step 3. In step 3, N-hydroxysuccinimid is added together with the matrix and 3,'3-diaminodipropylamine which reacts with the introduced amine group on the surface in dioxane.

Alternatives to the NHS method exist but the reaction conditions involve use of organic solvents and expensive chemicals.

Pavlovic et al. used electro contact printing to immobilize proteins in patterns on a thiolated flat silicon surface, by site-selective oxidation of thiols to thiolsulphinates (Nanoletters vol. 3, No. 6, 779-781, 2003).

WO 2009/074692 discloses a method for partially derivatizing a curved surface comprising electro-oxidation.

SUMMARY

It is an object of the present invention to alleviate at least some of the disadvantages of the prior art and to provide an improved method for immobilization of molecules comprising at least one amino group and to provide objects comprising such immobilized molecules.

In a first aspect there is provided a method for covalent immobilisation of at least one molecule comprising at least one amino group, said method comprising the sequential steps of:
a. providing a surface comprising —SH groups,
b. oxidising the surface comprising —SH groups by redox reactions in the presence of at least one noble metal ion, and
c. contacting the surface with at least one molecule comprising at least one amino group to obtain a covalent binding of the at least one molecule to the surface, wherein said at least one amino group is involved in obtaining said covalent bond.

In a second aspect, there is provided an object comprising at least one surface, wherein at least one molecule comprising at least one amino group is covalently bound to the surface, wherein at least one molecule is immobilized on the surface by the above method.

The inventors have carried out extensive research and found that groups which are formed by redox reactions involving thiol groups on a surface in the presence of noble metal ions such as Au-ions or Pt-ions result in formation of sulphur-Au clusters or sulphur-Pt clusters which are reactive in the next step towards thiols and amino-groups on molecules.

Advantages of the invention include that it is a more versatile technique for immobilization of molecules since the extra step to introduce thiol groups on the molecule can be eliminated and all reaction steps can be performed in aqueous solution.

A further advantage is that all steps can be performed at room temperature (about 20-25° C.).

Another advantage is that the covalent bonds formed during the redox reactions involving the groups on the surface and the amino groups are stable, even for single point attached molecules.

Yet another advantage is that the method can be performed with very few steps. If thiol groups are available on the surface from the start the process is a single step process. The method is easier to perform compared to methods according to the prior art.

Yet a further advantage is that the chemicals used are less expensive and less toxic compared to the prior art.

The redox process is fast, leading to formation of nanoclusters in seconds.

BRIEF DESCRIPTION OF THE DRAWINGS

The invention is described with reference to the following drawings in which.

DETAILED DESCRIPTION

Figure 1:
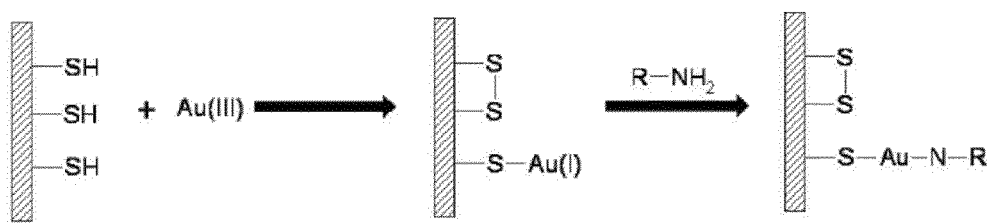
FIG. 1 shows an embodiment where —SH containing molecules on a surface in the presence of noble metal ions such as gold or platinum ions oxidize thiols to disulphides on the surface during formation of Au-sulphur nanoclusters which then immobilize a molecule comprising at least one amino group.

Before the invention is disclosed and described in detail, it is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The term "about" as used in connection with a numerical value throughout the description and the claims denotes an interval of accuracy, familiar and acceptable to a person skilled in the art. Said interval is ±10%.

As used throughout the claims and the description, the term "immobilization" in connection with molecules denotes the binding to a material. The present invention concerns covalent binding of the molecules to a base material.

As used throughout the claims and the description, the term "electro-oxidation" denotes oxidation by an applied external electric potential or current.

There is provided a method for immobilization of at least one molecule comprising at least one amino group, said method comprising the sequential steps of: a) providing a surface comprising —SH groups, b) oxidizing the surface comprising —SH groups in the presence of noble metal ions such as Au-ions or Pt-ions to the surface comprising —SH groups and c) contacting the surface with at least one molecule comprising at least one amino group to obtain a covalent binding of the at least one molecule to the surface, wherein said at least one amino group is involved in obtaining said covalent bond.

In one embodiment a surface comprising —SH groups is used as a start and in an alternative embodiment —SH groups are introduced on the surface.

In one embodiment the oxidation comprises electro-oxidation.

After the oxidation the surface is contacted with at least one molecule comprising at least one amino group. Thereby the amino group on the at least one molecule reacts and forms a covalent bond to the surface so that the at least one molecule is covalently bound to the surface.

In a second embodiment a surface comprising —SH groups is used as a start and in an alternative embodiment —SH groups are introduced on the surface. The surface is subsequently subjected to treatment with electro-oxidation. After the electro-oxidation the surface is contacted with at least one molecule comprising at least one amino group. Thereby the amino group on the at least one molecule reacts and forms a covalent bond to the surface so that the at least one molecule is covalently bound to the surface.

Without wishing to be bound to any particular scientific theory the inventors believe that redox reactions in the presence of noble metal ions such as gold or platinum ions oxidize thiols to disulphides on the surface during formation of eg. Au-sulphur nanoclusters.

In one embodiment at least a fraction of the —SH groups are reacted with each other before the step of oxidizing the surface. In one embodiment at least a fraction of the —SH groups are reacted to yield —S—S— bonds.

In one embodiment essentially all —SH groups are reacted with each other before the step of oxidizing the surface. By essentially all are meant that at least 99% of the number of molecules, preferably more than 99.9% are reacted.

In one embodiment the at least one molecule comprising at least one amino group is at least one molecule selected from the group consisting of molecules comprising at least one carbon atom, an amino acid, a peptide, a protein, an antibody, an aptamer, a virus, a virus fragment, a bacteria, a bacterial fragment, a cell, and a cell fragment. In one embodiment the at least one molecule comprising at least one amino group is at least one molecule selected from the group consisting of a protein, and an antibody.

In one embodiment the redox reaction is performed in an aqueous solution. In one embodiment the electro-oxidation is performed in a mixture of solvents.

In one embodiment the step of contacting the surface with at least one molecule comprising at least one amino group is performed in an aqueous solution. In one embodiment step of contacting the surface with at least one molecule comprising at least one amino group is performed in a mixture of solvents.

In one embodiment the method is performed at a temperature from 15° C. to 30° C. In an alternative embodiment the method is performed at room temperature about 20° C. to 25° C. In yet another embodiment the method is performed at a temperature from 5° C. to 45° C. In an alternative embodiment not comprising temperature-sensitive biomolecules the method is performed at a temperature up to several hundred degrees. In one embodiment the method is performed at a temperature from 15° C. to 300° C.

In one embodiment where electro-oxidation is used, the electro-oxidation is performed using a potential from 0.5 to 3 V in relation to a standard platinum electrode as a reference electrode. In one embodiment the electro-oxidation is performed using a potential from 0.1 to 5 V. In one embodiment the electro-oxidation is performed using a potential from 0.5 to 2 V. I another embodiment the electro-oxidation is performed using a potential from 0.5 to 1.5 V. In one embodiment the electro-oxidation is performed during a period of time from 1 second to 10 minutes. In an alternative embodiment the electro-oxidation is performed during a period of time from 0.1 second to 10 hours.

In one embodiment where electro-oxidation is used, the setup for electro-oxidation comprises a working electrode and a counter electrode. Optionally the setup further comprises a reference electrode adapted to measure the electric potential of the working electrode. In one embodiment at least one of the electrodes is coated with gold. In one embodiment at least one of the electrodes is adapted to rotate in the solution during the electro-oxidation. In one embodiment a fluid cell is constructed to obtain a large surface area of the working electrode where the electro-oxidation takes place.

In one embodiment the contacting of the surface with at least one molecule comprising at least one amino group is performed during a period of time from 10 minutes to 10 hours. In an alternative embodiment the electro-oxidation is performed during a period of time from 0.1 second to 72 hours.

In one embodiment the surface is subjected to derivatization to obtain functional groups on the surface, the functional groups which are finally obtained on the surface after derivatization are selected from —SH groups and —SS— groups. Preferably the surface is subjected to derivatization before the electro-oxidation.

In one embodiment a Na-acetate buffer with a pH of 4-5 is used.

In a second aspect there is provided an object comprising at least one surface, wherein at least one molecule comprising at least one amino group is covalently bound to the surface, wherein the at least one molecule is immobilized on the surface by the method described above.

In one embodiment the object is a particle. In one embodiment the object is a sensor. In one embodiment the object is a chromatographic separation medium. In one embodiment the object is a biomaterial. In one embodiment the object is a repair material for a tooth. In one embodiment the object is an object suitable for diagnostic purposes.

In one embodiment in which the object is a repair material for a tooth, one surface comprises thiols and is locally electro-oxidized, while the other surface comprises amino groups.

In one embodiment the method is used as a glue to join one surface comprising thiols which are oxidized and one surface comprising amino groups. In one embodiment there the object comprises at least one surface comprising oxidized thiol groups joined with at least one surface comprising amino groups.

In one embodiment the method is used for micro-contact printing and manufacture of microchips for protein arrays.

There is also provided use of a redox reaction to modify a surface comprising —SH groups in the presence of noble metal ions for subsequent covalent binding of at least one molecule comprising at least one amino group.

There is further provided use of at least one of surface bound Au—S cluster made by a redox reaction in the presence of a noble metal ions to immobilize a molecule comprising at least one amino group.

EXAMPLES

Example 1

Micromer -M PEG —$NH_2$

Commercially available monodisperse Micromer® -M particles (Micromod Partikeltechnologie GmbH) were used in these investigations. Each particle consists of a core of maghemite ($\gamma$-$Fe_2O_3$) nanoparticles embedded in a styrene-maleic acid-copolymer matrix with a surface coating consisting of crosslinked poly(methylmethacrylate-co-methacrylic acid) modified with bifunctional polyethylene glycol with amino function (—NH—($CH_2$—O—$CH_2$)$_{200}$—$NH_2$). The beads had an average diameter of 4.9 µm with a standard deviation of 0.2 µm. They were dispersed in water with a concentration of $7\times10^8$ particles/ml and with a magnetic material content of 50 mg/ml. The substitution grade was 5-6 nmol $NH_2$-groups per mg or $2.2\times10^8$ $NH_2$-groups per particle, according to the manufacturer.

Introduction of SS-pyridyl on Micromer -M PEG-$NH_2$

Micromer®-M PEG-$NH_2$ (100 µL, $7\times10^8$ particles/ml) was washed three times in 1000 µL PBS (10 mM phosphate, 150 mM NaCl, 10 mM EDTA, pH 7.4) and resuspended in 1000 µL PBS. N-Succinimidyl 3-(2-pyridyldithio)-propionate (SPDP) (25 µL, 20 mM in DMSO) was added to the bead suspension and reacted for 90 minutes. The beads were washed five times with 1000 µL PBS, resuspended in 1000 µL PBS and kept at 4° C.

Determination of SS-Pyridyl/Particle Ratio

Figure 2:
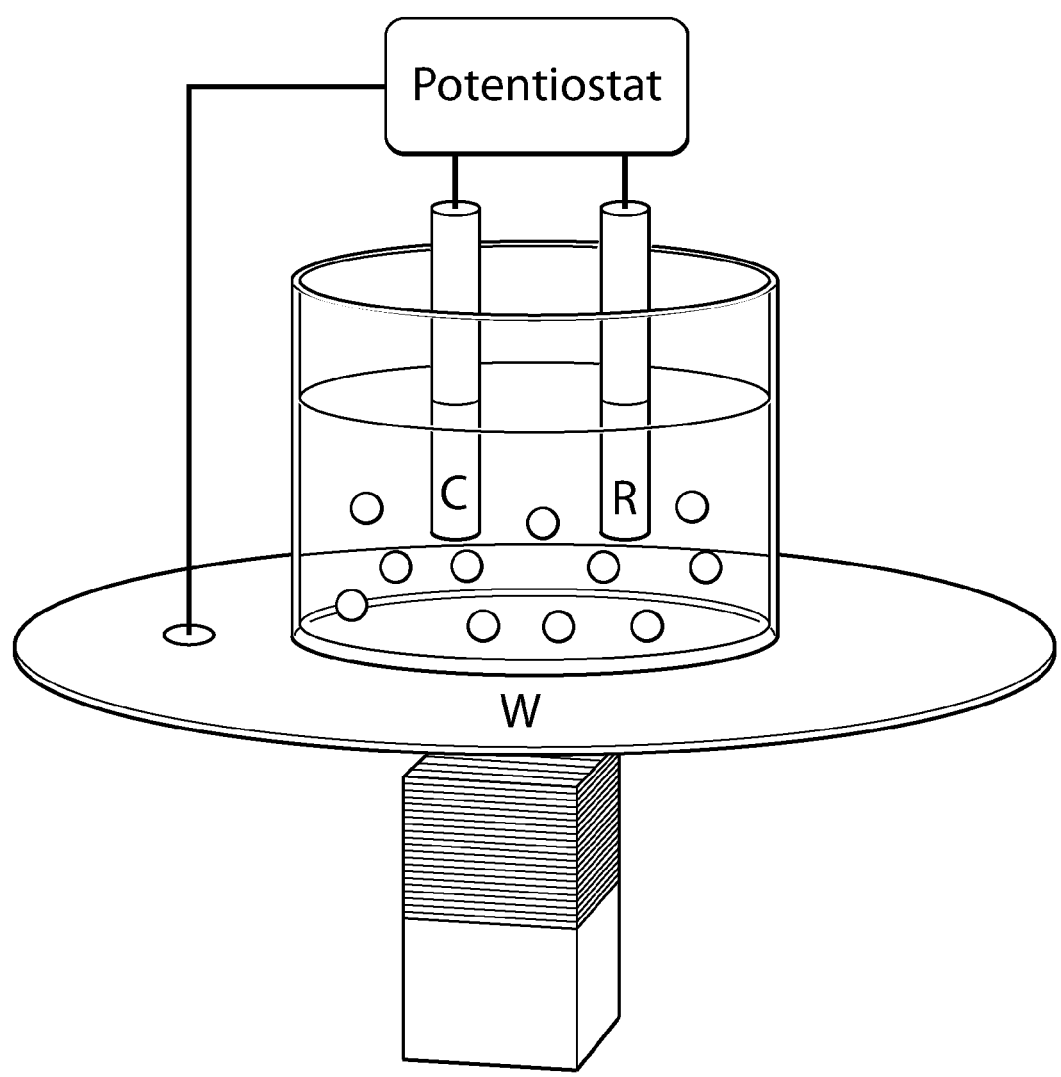
FIG. 2 shows a setup used in one embodiment for electro-oxidation of magnetic beads. Magnetic beads are attracted to the working electrode (W) by using a permanent magnet mounted underneath the electrode. A potential is applied between the working electrode and the reference electrode (R) employing a potentiostat, which also measures the current between the working electrode and the counter electrode (C).

Micromer -M PEG-SS-Pyridyl (100 µL, $7\times10^7$ particles) was mixed with 1000 µL dithiothreitol (DTT) in PBS containing 2% w/v DTT and incubated at room temperature for 20 min. Particles were collected with a magnet and the supernatant was further used in spectrophotometric analyses of the SS-pyridyl content (FIG. 2) were determined by spectrophotometry, using a Shimadzu (Kyoto, Japan) UV-2101 PC spectrophotometer and quarts cuvettes, at wavelength 343 nm ($\varepsilon$=8080 $M^{-1}$ $cm^{-1}$). About $1.0\times10^8$ SS-pyridyl groups were attached to each particle.

Preparation of Micromer -M PEG-SH

Immediately prior to electro-oxidation, the Micromer -M PEG-SS-Pyridyl particles in 1000 µl suspension ($7\times10^7$ particles/ml) were collected with an external magnet and the buffer was changed to 1000 µL dithiothreitol (DTT) in acetate buffer (pH 4.5, 2% w/v DTT) and incubated at room temperature for 20 min. The beads were washed five times with PBS (10 mM phosphate, 150 mM NaCl, pH 7.4), resuspended in 80 ml PBS to a final concentration of $8.75\times10^6$ particles/ml and kept at room temperature.

Preparation of Agarose —SH Particles

Sepharose 6B was washed with distilled water on a glass filter and sucked dry. 3 g dry gel particles were suspended in 2.4 ml 1M sodium hydroxide solution and epichlorohydrin 0.45 ml was added drop wise under stirring under room temperature. The temperature was increased to 60° C. and maintained for 2 hours. The sepharose gel was washed with distilled water until neutral on a glass filter. Further the epoxide activated gel (3 g) was washed on the glass filter with 50 ml 0.5M phosphate buffer pH 6.3 and sucked dry. The gel was resuspended in the phosphate buffer (6 ml). 3 ml of 2M sodium thiosulphate was added and the mixture was shaken for 6 hours at room temperature. Excess sodium thiosulphate was washed out from the thiosulphate ester gel with distilled water. In order to prepare a thiolated gel the thiosulphate ester gel was reduced with dithiothreitol (DTT). 1 g of the thiosulphate ester gel was washed on a glass filter and suspended in 3 ml of 0.1M sodium bicarbonate solution. 0.1 g DTT in 2 ml (1 mM) EDTA solution was added and the ester gel was reduced for 30 minutes. The reduced gel was washed with 30 ml 0.1M sodium bicarbonate solution (1M sodium chloride and 1 mM EDTA) and finally with 100 ml 1 mM EDTA solution. The thiolated Sepharose 6B particles were suspended in 10 mM sodium phosphate buffer.

Experimental Setup for Electro-Oxidation

The reaction cell used for electro-oxidation of particles consisted of a teflon cylinder mounted on top of a gold-plate. A vertical magnetic field was applied by using a permanent magnet mounted underneath the gold-plate (350 mT at the inner surface of the gold-plate). The counter- and reference-electrodes were mounted inside the reaction cell and the gold-plate acting as working electrode was connected outside the reaction cell (see FIG. 2)

Electro-Oxidation of Thiols on Particles

Before experiments, the reaction cell and the working electrode were cleaned in a mixture of 7.5 ml of 30% (w/v) hydrogen peroxide (Merck Inc., P.A. grade) and 15 ml sulfuric acid (P.A. Grade) followed by water rinsing. Thiolated particles, 0.75 mg or 0.25 mg magnetic particles or 2-6 mg agarose particles, in 3 ml PBS were then added to the reaction cell. Particles were allowed to distribute on the gold surface by the forces of gravity (agarose particles) and magnetic field (magnetic particles) for 5 min. Potentials spanning 0.45-0.90 V versus the Ag/AgCl reference electrode were applied for 1 s. Between different oxidations of thiolated beads the working counter and reference electrodes were washed with PBS. The particles were thereafter resuspended and the volume reduced to 200 µL by collecting magnetic particles with a permanent magnet and agarose particles by centrifugation. Prior to the measurements, a cyclic voltammogram (−0.2 to +1.5 V, 50 mV/s) was recorded in the PBS solution in the absence of particles to verify that the gold working electrode was working properly.

Conjugation of Biomolecules to Electro-Oxidized Particles

The particle suspension from the electro-oxidation experiments was mixed with 100 µL biomolecules (IgG, β-alanine, α-lactalbumin, α-lactalbumin(FITC) and protein A) (2 mg/ml in PBS) and incubated for 40 minutes. Unbound biomolecules was removed by washing the particles in approximately 10 ml PBS. Reactions were evaluated with respect to the degree of fluorescence of the particle surface and with amino acid analysis. Fluorescence was evaluated with a Nikon Eclipse fluorescence microscope equipped with a Nikon Coolpix camera. The fluorescence filter was tuned to provide an excitation wavelength of 494 nm and an emission wavelength of 520 nm. Amino acid analyses were performed according to an improved version of the classical method developed by Spackman, Stein and Moore, by which elimination of ammonia by use of special filters allow separation of all amino acids on a 4.6×200 mm high resolution PEEK column with Ultrapac 8 resin (Biachrome). The amount of amino acid was detected at two different wave lengths, 440 nm and 570 nm, by use of Biachrome 20 and Biachrome 30 analytical instruments. Limit of detection is 25-50 pmol and limit of quantification is 50-100 pmol. 2 ml of 6 M HCl (containing an internal standard) was added to a fixed volume of particle suspension of known weight, which was then hydrolysed at 100° C. during 24 h. The agarose particles were freeze dried before amino acid analysis.

Example 2

Study of Different Potential During Electro-Oxidation

The immobilized molecules were homogeneously distributed all over the bead surface investigated by use of FITC marked molecules. The capacity to bind molecules is dependent of the voltage applied during the electro-oxidation step (see table 1a) with an unspecific adsorption of molecules at zero voltage and a maximum at a voltage of 0.9 V. The results shown in table 1 indicate that it is possible to regulate the substitution degree of molecules on the particles both by the voltage applied and the particle concentration The binding capacity of biomolecules were investigated on agarose (Sepharose 6B) and was found to be 29.4 mg IgG per g freeze dried agarose.

TABLE 1a

| Potential, V | Mass of particles (mg) | biomolecule | Capacity mg/particle |
|---|---|---|---|
| 0.9 | 0.75 | IgG | 3.5 |
| 0.75 | 0.75 | IgG | 2.2 |
| 0.45 | 0.75 | IgG | 1.8 |

The capacity to bind α-lactalbumin to agarose was investigated for different voltages. The electrooxidation was performed during 60 seconds. An amino acid analysis was performed to calculate the amount of bound α-lactalbumin. See the results in table 1b.

TABLE 1b

| Potential, V | Mass in mg of α-lactalbumin per weight in g of dry agarose | biomolecule |
|---|---|---|
| 0 | 1.23 mg/g | α-lactalbumin |
| 0.5 | 0.91 mg/g | α-lactalbumin |
| 1.0 | 51.96 mg/g | α-lactalbumin |
| 1.5 | 28.7 mg/g | α-lactalbumin |
| 2.0 | 26.0 mg/g | α-lactalbumin |

Example 3

Stability Studies

In order to investigate the stability of bonds between the surface and the immobilized biomolecule, IgG and β-alanine was immobilized to electro-oxidized magnetic particles. The particles were washed extensively with a large excess of phosphate buffered saline at pH 7.2 during hours and amino acid analyses were performed before and after this extensive washing procedure.

The stability for immobilized IgG and β-alanine on magnetic particles after extensive washing is 100% respectively 75%, see table 2a.

Stability of the reactive sulphur/Au complex on the surface of magnetic particles was investigated by storage of freshly electro-oxidized particles for 30 days in dioxane and etanol (50% v/v in distilled water) before attachment of IgG, see table 2b. The reactive structures formed in electro-oxidation shows 66% respectively 42% stability.

Investigation of stability of the reactive sulphur/Au complex on agarose formed during electro-oxidation. Agarose was electro-oxidized at 1.0 V for 60 s. Half of the agarose was reacted with α-lactalbumin, as a reference sample, and the other half was stored in acetate buffer pH 5. After 40 days the acetate buffer was removed and α-lactalbumin was added. Amino acid analyses were performed on both samples. The reference sample obtained 31 mg α-lactalbumin per g dry agarose while the agarose particles stored in acetate buffer obtained 27 mg α-lactalbumin per g dry agarose. Hence, the reactivity of the sulphur/Au complex was 88% after storage in acetate buffer.

TABLE 2a and 2b

A upper part, stability of bonds for IgG and β - alanine immobilized to electro-oxidized magnetic particles. B lower part, stability of the reactive structures on particle surface in dioxane and ethanol 50% before attachment of IgG.

| Potential, V | Mass of particles, mg | biomolecule | PBS wash, ml | Capacity mg/particle | Stability % |
|---|---|---|---|---|---|
| 0.9 | 0.75 | IgG | 10 | 3.6 | 100 |
| 0.9 | 0.75 | IgG | 50 | 3.6 | 100 |
| 0.9 | 0.75 | β - alanine | 10 | 0.8 | 100 |
| 0.9 | 0.75 | β - alanine | 50 | 0.6 | 75 |

| Potential, V | Mass of particles, mg | Storage media | Days | Capacity mg/particle | Stability % |
|---|---|---|---|---|---|
| 0.9 | 0.25 | PBS | 0 | 7.4 | 100 |
| 0.9 | 0.25 | Dioxane | 30 | 4.9 | 66 |
| 0.9 | 0.25 | Ethanol 50 wt % | 30 | 3.1 | 42 |

Example 4

Stability Studies at Low pH

In order to investigate the stability at low pH of immobilized proteins to electrochemical oxidized agarose, protein A and IgG was successfully immobilized as described above. Thereafter, the agarose-protein particles were treated with glycine buffer, pH 3 for 20 minutes. As shown in table 3 the bond between immobilized protein A and IgG was stable for at least 20 minutes at pH 3. It can be concluded that the immobilized molecules are stable at low pH.

TABLE 3

IgG and protein A immobilized on electro-oxidized thiol agarose particles for investigation of the stability of bonds between protein A and agarose at pH 3.

| Potential, V | Mass of agarose, mg | biomolecule | Capacity mg/particle |
|---|---|---|---|
| 0.9 | 2.01 | IgG | 29.4 |
| 0.9 | 2.01 | Protein A | 3.2 |
| 0.9 | 2.01 | Protein A washed with glycine buffer pH 3 for 20 minutes | 7.8 |

Example 5

Comparison Between Chemical Oxidation and Electro-Oxidation of Agarose-SH Particles Chemical Oxidation with Hydrogen Peroxide.

2 mg of thiolated agarose particles was oxidized in 2 ml 3.5% $H_2O_2$ in acetate buffer pH 5 for 20 hours. After the oxidation particles were washed on a glass filter with 10 ml PBS. Biomolecules, 500 µl alactalbumin(FITC) (2 mg/ml in PBS) was added to the oxidized agarose —SH particles. The reaction was evaluated after 40 minutes and after 24 hours with respect to the degree of fluorescence of the particle surface. After 40 minutes no fluorescence was found. After 24 hours weak fluorescence, which was visible in the fluorescence microscope with 200 times magnification, appeared on the particle surface. Compare to electro-oxidized agarose —SH particles, where the fluorescence of alactalbumin (FITC) is visible with your naked eye after 40 minutes, this is a non efficient technique for immobilization of native biomolecules on agarose particles.

Chemical oxidation with hydrogen peroxide and gold(III) chloride. 8 mg of thiolated agarose particles were oxidized in 10 ml 3.5% $H_2O_2$ in acetate buffer pH 5 for 12 hours. After the oxidation particles were washed on a glass filter with 50 ml PBS. Particles were than mixed with a solution of 10 ml gold(III) chloride (8 mM in PBS) for 2 minutes. Particles were washed on a glass filter with 100 ml PBS and then mixed with biomolecules, 500 µl a lactalbumin(FITC) (2 mg/ml in PBS) for 40 minutes. Particles were then again washed on a glass filter with 50 ml PBS. The particles shows strong homogeneous fluorescence indicating that the biomolecules is successfully immobilized onto the agarose particles.

Chemical Oxidation with Gold(III) Chloride. 8 mg of thiolated agarose particles were mixed with a solution of 10 ml gold(III) chloride (8 mM in PBS) for 2 minutes. Particles were washed on a glass filter with 100 ml PBS and then mixed with biomolecules, 500 µl alactalbumin(FITC) (2 mg/ml in PBS) for 40 minutes. Particles were then again washed on a glass filter with 50 ml PBS. The particles shows strong homogeneous fluorescence indicating that the biomolecules is successfully immobilized onto the agarose particles.

TABLE 4

Shows the content of gold, after different oxidation procedures, and alactalbumin(FITC) (LALBA) after biomolecule immobilization on oxidized agarose -SH particles. e. Ox is electro oxidation as described above during 60 seconds at 1.0 volt, C. Ox Agarose (AuCl3) is chemical oxidation with gold(III) chloride and C. Ox Agarose (H2O2/AuCl3) is chemical oxidation with hydrogen peroxide and gold(III) chloride. 8 mg of agarose - SH particles is oxidized in all cases. Gold content is measured with ICP and the LALBA content is determined with amino acid analysis.

| Sample | µg Au | µmol Au | µg LALBA | nmol LALBA |
|---|---|---|---|---|
| e. Ox Agarose-SH | 80.3 | 0.407614 | 176 | 12.57143 |
| C. Ox Agarose (AuCl3) | 729.7 | 3.704061 | 296.8 | 21.2 |
| C. Ox Agarose (H2O2/AuCl3) | 372.3 | 1.889848 | 218.1 | 15.57857 |

The invention claimed is:

1. A method for covalent immobilisation of at least one molecule comprising at least one amino group, said method comprising the sequential steps of:

a. providing a surface comprising —SH groups,
b. oxidising the surface comprising —SH groups by redox reactions in the presence of at least one noble metal ion, and
c. contacting the surface with at least one molecule comprising at least one amino group to obtain a covalent binding of the at least one molecule to the surface, wherein said at least one amino group is involved in obtaining said covalent bond.

2. The method according to claim 1, wherein the at least one noble metal ion is selected from the group consisting of Au and Pt.

3. The method according to claim 1, wherein the redox reaction yields at least one functional group on the surface, and wherein the at least one functional group is selected from the group consisting of thiols, disulphides, thiolsulfinate groups and thiolsulfonate groups.

4. The method according to claim 3, wherein the functional group on the surface, reacts with the noble metal ion.

5. The method according to claim 1, wherein at least a fraction of the —SH groups are reacted with each other before the step of oxidising the surface using redox reactions.

6. The method according, to claim 1, wherein essentially all —SH groups are reacted with each other before the step of oxidising the surface using redox reactions.

7. The method according to claim 1, wherein the at least one molecule comprising at least one amino group is selected from the group consisting of a molecule comprising a carbon atom, an amino acid, a peptide, a protein and an aptamer.

8. The method according to claim 1, wherein the at least one molecule, comprising at least one amino group is at least one molecule selected from the group consisting of a protein and an antibody.

9. The method according to claim 1, wherein the redox reaction is performed in an aqueous solution.

10. The method according to claim 1, wherein the redox reaction is performed in a mixture of solvents.

11. The method according to claim 1, wherein the step of contacting the surface with at least one molecule comprising at least one amino group is performed in an aqueous solution.

12. The method according to claim 1, wherein the step of contacting the surface with at least one molecule comprising at least one amino group is performed in a mixture of solvents.

13. The method according to claim 1, wherein the method is performed at a temperature from 15° C. to 300° C.

14. The method according to claim 1, wherein said redox reaction comprises electrooxidation, and wherein the electrooxidation is performed using a potential from 0.5 to 3 V.

15. The method according to claim 1, wherein said redox reaction comprises electrooxidation, and wherein the electrooxidation is performed during a period of time from 1 second to 10 minutes.

16. The method according to claim 1, wherein the contacting of the surface with at least one molecule comprising at least one amino group is performed during a period of time from 10 minutes to 10 hours.

17. The method according to claim 1, wherein the surface is subjected to derivatization to obtain functional groups on the surface, wherein the functional groups are selected from the group consisting of —SH groups and —SS— groups.

18. A method for modifying a surface comprising —SH groups, the method comprising conducting a redox reaction on a surface comprising —SH groups in the presence of noble metal ions to form sulfur-metal ion complexes or clusters which are reactive with amino groups to form covalent bonds for subsequent covalent binding of at least one molecule comprising at least one amino group.

19. A method for immobilizing a molecule comprising at least one amino group, comprising covalently binding the amino group with at least one of surface bound thiolsulfinate and a surface bound thiolsulfonate made by a redox reaction in the presence of a noble metal ion.

* * * * *

UNITED STATES PATENT AND TRADEMARK OFFICE
CERTIFICATE OF CORRECTION

PATENT NO. : 8,679,807 B2
APPLICATION NO. : 13/812101
DATED : March 25, 2014
INVENTOR(S) : Sven Oscarsson et al.

Page 1 of 1

It is certified that error appears in the above-identified patent and that said Letters Patent is hereby corrected as shown below:

In the Claims

Claim 7, Column 11, Line 29, after "protein", insert --, antibody--.

Signed and Sealed this
First Day of July, 2014

Michelle K. Lee
*Deputy Director of the United States Patent and Trademark Office*